US009924872B2

(12) United States Patent
Harada

(10) Patent No.: US 9,924,872 B2
(45) Date of Patent: Mar. 27, 2018

(54) COMPUTED TOMOGRAPHY APPARATUS

(75) Inventor: Tomokazu Harada, Irvine, CA (US)

(73) Assignee: Toshiba Medical Systems Corporation, Otawara-shi (JP)

( * ) Notice: Subject to any disclaimer, the term of this patent is extended or adjusted under 35 U.S.C. 154(b) by 34 days.

(21) Appl. No.: 14/113,696

(22) PCT Filed: Jun. 13, 2012

(86) PCT No.: PCT/JP2012/065163
§ 371 (c)(1),
(2), (4) Date: Oct. 24, 2013

(87) PCT Pub. No.: WO2012/173157
PCT Pub. Date: Dec. 20, 2012

(65) Prior Publication Data
US 2014/0056401 A1 Feb. 27, 2014

(30) Foreign Application Priority Data
Jun. 14, 2011 (JP) .................. 2011-132395

(51) Int. Cl.
*A61B 5/00* (2006.01)
*A61B 6/08* (2006.01)
(Continued)

(52) U.S. Cl.
CPC ............ *A61B 5/0073* (2013.01); *A61B 6/032* (2013.01); *A61B 6/08* (2013.01); *A61B 6/545* (2013.01); *A61B 6/027* (2013.01)

(58) Field of Classification Search
None
See application file for complete search history.

(56) References Cited

U.S. PATENT DOCUMENTS 4,416,022 A 11/1983 Cutter
4,618,980 A * 10/1986 Lescrenier ............... G21K 1/04
378/205

(Continued)

FOREIGN PATENT DOCUMENTS

CN 101072540 A 11/2007
JP 61-276546 A 12/1936
(Continued)

OTHER PUBLICATIONS

Combined Office Action and Search Report dated Jan. 20, 2015 in Chinese Patent Application No. 201280020953.3 (with English translation of categories of cited documents).
(Continued)

*Primary Examiner* — Hoon Song
(74) *Attorney, Agent, or Firm* — Oblon, McClelland, Maier & Neustadt, L.L.P.

(57) ABSTRACT

A computed tomography apparatus capable of confirming the positional relationship of an imaging region and a field of view in a real space at the time of determining the position of the imaging region. The computed tomography apparatus according to an embodiment comprises a couch that moves a top board on which a subject is placed. A gantry comprises an opening into which a top board is inserted. A light projection part is provided in the gantry. A setting part sets a field of view with respect to the subject. A controller causes light indicating the set field of view to be projected by controlling the light projection part.

12 Claims, 18 Drawing Sheets

(51) Int. Cl.
    *A61B 6/03*    (2006.01)
    *A61B 6/00*    (2006.01)
    *A61B 6/02*    (2006.01)

(56) References Cited

U.S. PATENT DOCUMENTS

| | | |
|---|---|---|
| 4,836,671 A | 6/1989 | Bautista |
| 5,577,095 A | 11/1996 | Kobayashi |
| 2003/0071128 A1 | 4/2003 | Tsikos et al. |
| 2005/0013410 A1 | 1/2005 | Hornegger |
| 2007/0036274 A1* | 2/2007 | Haras et al. ............... 378/206 |
| 2008/0181359 A1* | 7/2008 | Stayman ............... A61B 6/032 |
| | | 378/20 |
| 2009/0252290 A1 | 10/2009 | Plut et al. |

FOREIGN PATENT DOCUMENTS

| | | |
|---|---|---|
| JP | 54-99515 A | 8/1979 |
| JP | 07 023942 | 1/1995 |
| JP | 7 148160 | 6/1995 |
| JP | 2001 224583 | 8/2001 |
| WO | WO 2009/093187 A1 | 7/2009 |

OTHER PUBLICATIONS

Office Action dated Mar. 15, 2016 in Japanese Patent Application No. 2012-134283.
International Search Report dated Sep. 11, 2012 in PCT/JP12/065163 Filed Jun. 13, 2012.

* cited by examiner

COMPUTED TOMOGRAPHY APPARATUS

FIELD OF THE INVENTION

Embodiments of the present invention are related to a computed tomography apparatus.

BACKGROUND OF THE INVENTION

A computed tomography (CT) apparatus is an apparatus for imaging the inside of an object by scanning the object using radiation, etc. and processing the acquired data using a computer. Some examples of CT apparatuses include: an X-ray CT apparatus, PET (Positron Emission Tomography), SPECT (Single Photon Emission Computed Tomography), an MRI (Magnetic Resonance Imaging) apparatus, etc.

The computed tomography apparatus comprises a gantry, a couch, a console, etc. The gantry is provided with an opening in the center region thereof. A subject placed on the couch is moved into the inside of the opening and subjected to an examination. At that time, a light beam from a projector provided in the gantry is used to estimate the body axis of the subject in order to perform determination of the position of the center of the opening and the subject (determination of the position of an imaging region).

Furthermore, a field of view is set when conducting computed tomography imaging. The "field of view" is the region in which imaging by a computed tomography apparatus is possible. Because the field of view varies depending on the imaging conditions (imaging region, etc.), in general, several fields of view are preliminarily set and stored for each apparatus. The field of view preferably covers the entire imaging region (for example, a head or a torso) including a region of interest of the subject. Moreover, by setting the range of the field of view to be approximately the same size as the imaging region of the subject, imaging with high resolution becomes possible with the apparatus.

PRIOR ART DOCUMENT

Patent Document

[Patent Document 1] Japanese published unexamined application H7-23942

SUMMARY OF THE INVENTION

Problem to be Solved by the Invention

However, conventional computed tomography apparatuses are not capable of confirming the positional relationship between the imaging region and the field of view in a real space when determining the position of the imaging region. Therefore, in the case of a subject with a large body size, etc., it is possible to end up imaging when the imaging region is not located within the field of view.

On the contrary, in the case of a subject with a small body size with respect to a set field of view, there is a possibility of radiation also being irradiated on portions not required for imaging. Therefore, there is a problem of increased exposure.

The problem that the present invention is intended to solve is to provide a computed tomography apparatus capable of confirming the positional relationship between an imaging region and a field of view in a real space at the time of determining the position of the imaging region.

Means of Solving the Problem

A computed tomography apparatus in an embodiment images the inside of a subject by processing, using a computer, data acquired by irradiating radiation onto the subject. A couch moves a top board on which the subject is placed. A gantry comprises an opening into which the top board is inserted. A light projection part is provided in the gantry. A setting part sets the field of view with respect to the subject. A controller causes light indicating the set field of view to be projected by controlling the light projection part.

DESCRIPTION OF THE PREFERRED EMBODIMENT

<Embodiment 1>

The configuration of the computed tomography apparatus pertaining to Embodiment 1 is described with reference to FIGS. 1 through 6. The present embodiment describes an X-ray CT apparatus 1 as a computed tomography apparatus. The X-ray CT apparatus 1 is an image diagnostic device by which the penetration of X-rays radiated onto a subject 2 is detected and the inside images of the subject body are reconstructed from the projection data indicating the intensity of the detected X-rays.

<Apparatus Configuration>

Figure 1:
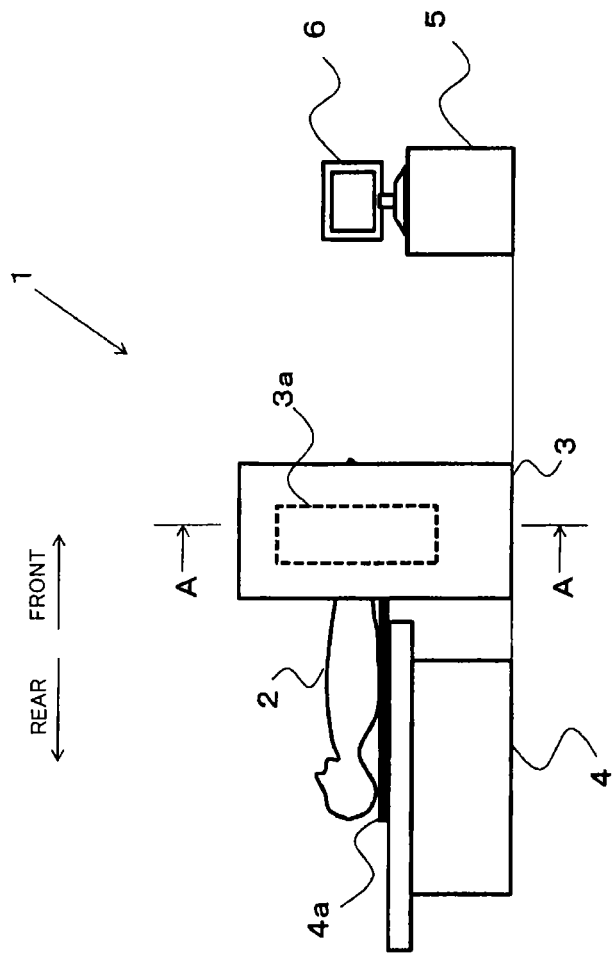
FIG. 1 is an appearance drawing of an X-ray CT apparatus pertaining to Embodiment 1.

As shown in FIG. 1, the X-ray CT apparatus 1 comprises a gantry 3, a couch 4, a console 5, and a display 6.

<Gantry>

Figure 3:
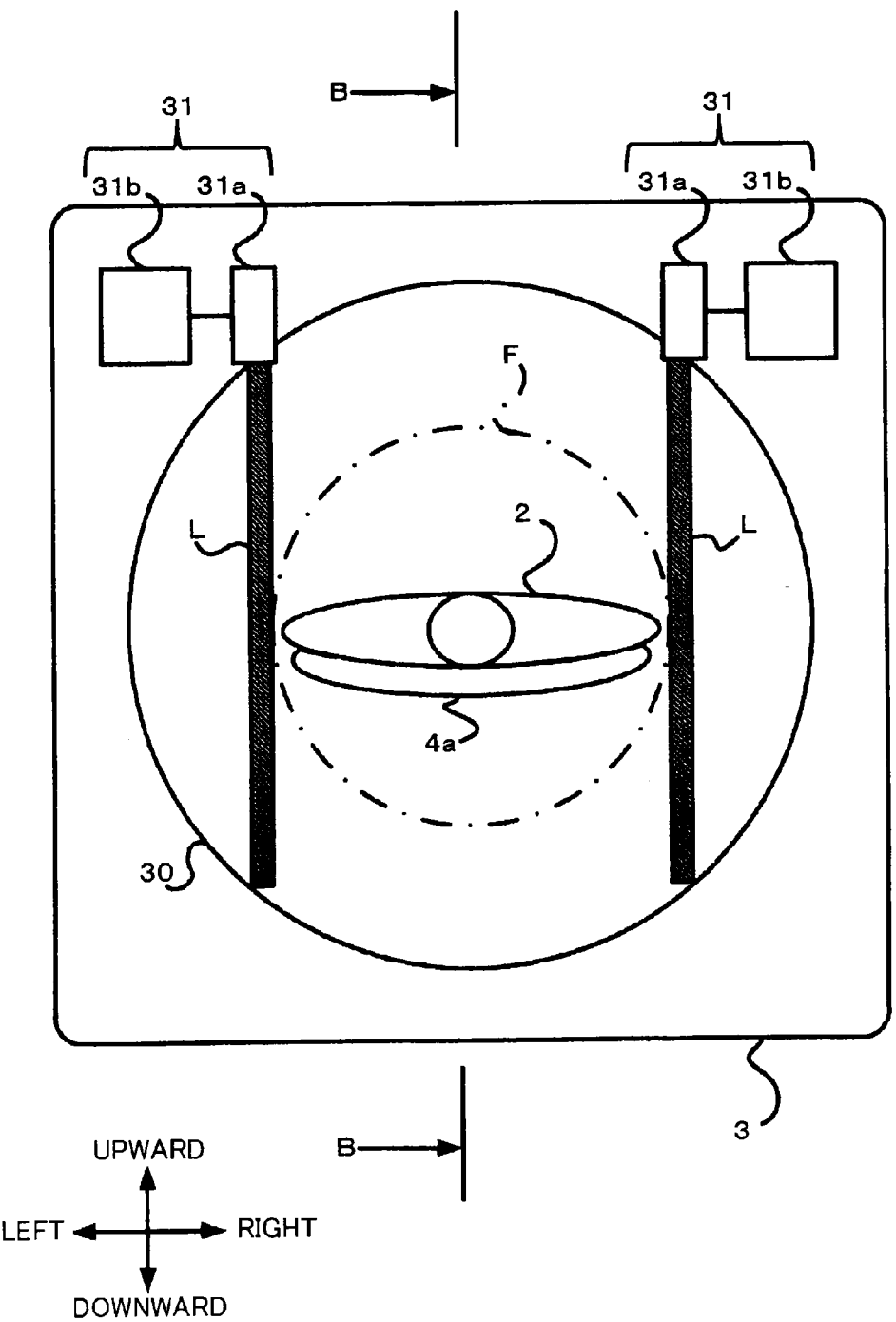
FIG. 3 is a drawing showing the configuration of a gantry pertaining to Embodiment 1.

The gantry 3 performs radiation of X-rays and detection of X-rays penetrating through the subject 2. An X-ray radiation part (not illustrated), an X-ray detector (not illustrated), and a light projection part 31 (described later) are arranged inside the gantry 3. The X-ray radiation part irradiates X-rays with respect to the subject 2 when high voltage is applied from a high voltage generator (not illustrated). The X-ray detector detects X-rays penetrating through the subject 2. The gantry 3 comprises an opening 30 (ref. FIG. 3, etc.) into which a top board 4*a* (described later) is inserted. Furthermore, the gantry 3 comprises an operation part (not illustrated) for inputting various kinds of operations.

A rotation base 3*a* wherein the X-ray radiation part, the X-ray detector, and the light projection part 31 are arranged is provided in the gantry 3 (ref. FIG. 1). Furthermore, a drive mechanism (not illustrated) for rotating the rotation base 3*a* around the subject 2 is provided in the gantry 3. The rotation base 3*a* and the drive mechanism are one example of a "rotation mechanism." It should be noted that it is sufficient for the rotation mechanism to be configured such that it is capable of rotating at least the light projection part 31.

<Couch>

The couch 4 comprises the top board 4*a*. The subject 2 is placed on the top board 4*a*. The couch 4 comprises a mechanism for moving the top board 4*a* on which the subject 2 is placed, based on an instruction from a controller 52 (described later).

<Console>

The console 5 performs various kinds of operation controls of the X-ray CT apparatus 1 and processes. For example, the console 5 controls operations such as X-ray irradiation start/stop by the X-ray radiation part and rotation start/stop by the rotation mechanism. Furthermore, the console 5 processes the detected data of X-rays by the gantry 3 and reconstructs the images inside the subject 2. The console 5 comprises an operation part (not illustrated) for inputting various kinds of operations.

<Display>

The display 6 is connected to the console 5 and displays images reconstructed by the console 5. Furthermore, the display 6 displays various kinds of screens such as a set-up screen, etc. of the apparatus and information regarding a patient.

Figure 2:
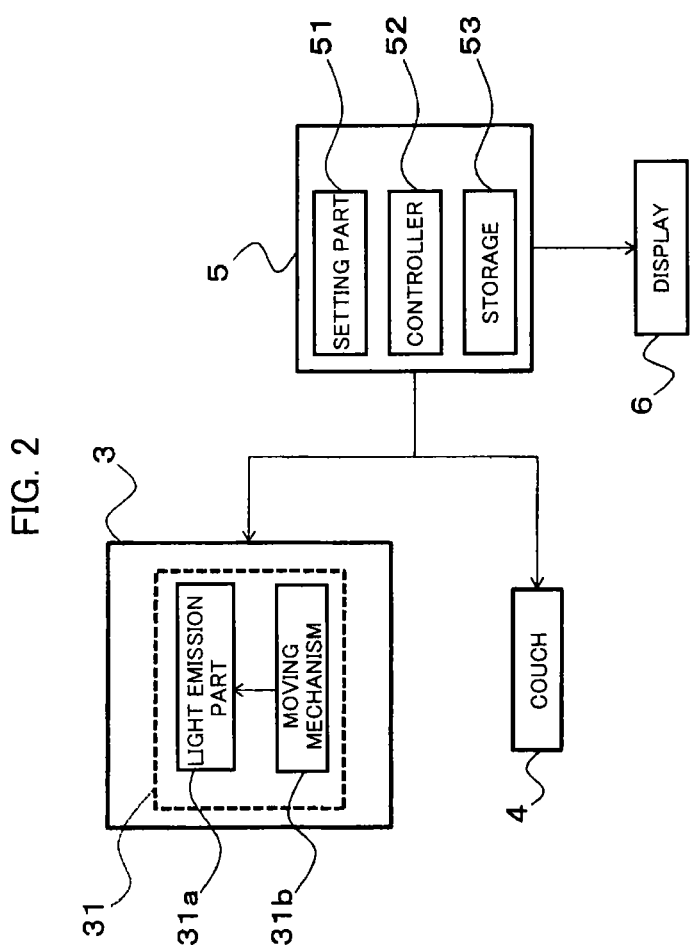
FIG. 2 is a block diagram showing the internal configuration of the X-ray CT apparatus pertaining to Embodiment 1.
Figure 4:
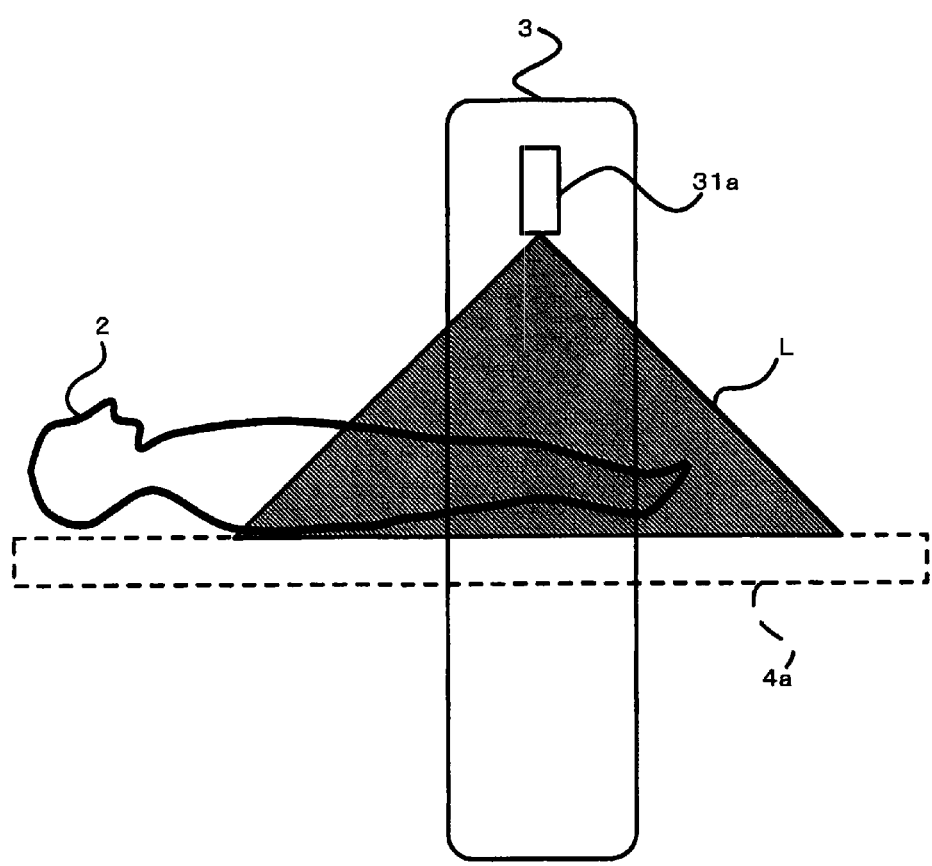
FIG. 4 is a drawing showing the configuration of a gantry pertaining to Embodiment 1.

Next, the internal configuration of the computed tomography apparatus pertaining to Embodiment 1 is described with reference to FIGS. 2 through 4. FIG. 3 shows a cross-section A-A of the gantry 3 in FIG. 1. FIG. 4 shows a cross-section B-B of the gantry 3 in FIG. 3. FIG. 3 and FIG. 4 represent a state in which light L is irradiated from the light projection part 31 (described later). In the present embodiment, the foot side of the subject 2 placed on the top board 4*a* is regarded as the "front" direction while the head side of the subject 2 is regarded as the "rear" direction. Furthermore, the directions when the gantry 3 is seen from the couch 4 side (for example, ref. FIG. 3) are respectively regarded as the "upward, downward, left and right" directions.

The gantry 3 comprises light projection parts 31. The light projection part 31 projects light L in the prescribed direction. The light L from the light projection part 31 is, for example, a laser beam. In the present embodiment, as shown in FIG. 3, two light projection parts 31 are provided sandwiching the center of the opening 30 in the upper part of the gantry 3.

The light projection part 31 comprises a light emission part 31*a* and a moving mechanism 31*b*.

The light emission part 31*a* is a light source for generating light L. The light emission part 31*a* in the present embodiment generates light heading in the downward direction from the upward direction and spreading in the front and rear directions from the light emission part 31*a* while maintaining a constant width in the left and right directions (ref. FIG. 3 and FIG. 4).

The moving mechanism 31*b* moves the light emission part 31*a* in the left and right directions. The moving mechanism 31*b* is, for example, an electric actuator composed of a motor and a gear, etc. The operation control of the moving mechanism 31*b* is conducted by the controller 52 (described later).

Start/stop of light generation by the light emission part 31*a* and the operation of the moving mechanism 31*b* are controlled by the controller 52 (described later). Alternatively, manual operation by an examiner is also possible from switches provided in the gantry 3, etc.

It should be noted that the configuration of the light emission part 31*a* is not limited to the above configuration. As the light projected from the light emission part 31*a* becomes wider in the front and rear directions, the light L is projected with more reliability with respect to the subject 2. Therefore, for example, it is also possible to project rectangular-shaped light L from a light source which is long in the front and rear directions. Alternatively, it is also possible to configure such that the light emission part 31*a* is scanned in the longitudinal direction (the front and rear directions) of the top board 4*a* by using a light source to generate line-shaped light L as the light emission part 31*a*. This scanning is, for example, conducted by the moving mechanism 31*b*.

Furthermore, the number or position of the light projection parts 31 (light emission part 31*a*, moving mechanism 31*b*) is not limited to the above configuration. For example, it is sufficient to provide at least one light projection part 31. Moreover, the light projection part 31 may be provided in the lower part of the gantry 3 or may be provided in a manner projecting outside the gantry 3.

The console 5 comprises a setting part 41, the controller 52, and storage 53.

The setting part 51 sets the field of view F with respect to the subject 2. As for the field of view F, several values (for example, the radius of the field of view) are preliminarily stored in the storage 53. It should be noted that the storage 53 may store a wider range (for example, a radius of the field of view +1 mm) or a narrower range (for example, a radius of the field of view −1 mm) than the actual field of view as a value of the field of view F. That is, the "field of view F" in the present embodiment is a concept including the actual field of view and the neighborhood region thereof. The setting part 51 selects the value corresponding to an instruction input by the examiner from a plurality of values stored in the storage 53, and sets the field of view F based on this value.

The controller 52 projects light L indicating the field of view F set by the setting part 51 by controlling the light projection part 31. Specifically, by controlling the moving mechanism 31*b* based on the field of view. F that has been set by the setting part 51, the controller 52 moves the light emission part 31a and projects the light L from the light emission part 31a such that the light L touches the outer circumference of the field of view F. For example, in the case of a field of view F with a distance r from the center position of the opening 30 as the radius, the controller 52 controls the moving mechanism 31b and moves the light emission part 31a from an initial position (the position where the light emission part 31a is arranged at the time of starting the apparatus; which is defined as the default) to the position r. Then, the controller 52 causes the light emission part 31a to emit light at this position, the light L touching the outer circumference of the field of view F is projected.

<Operation>

Figure 5:
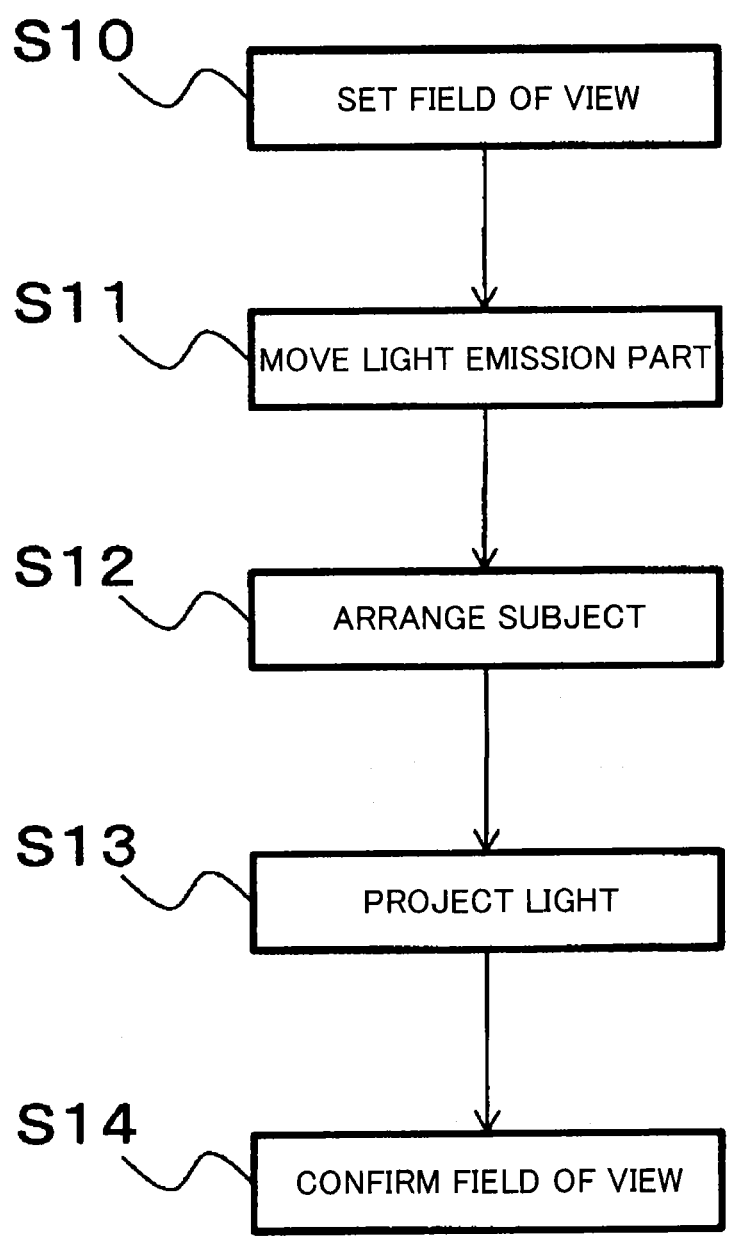
FIG. 5 is a flow chart showing the outline of the processing pertaining to Embodiment 1.
Figure 6:
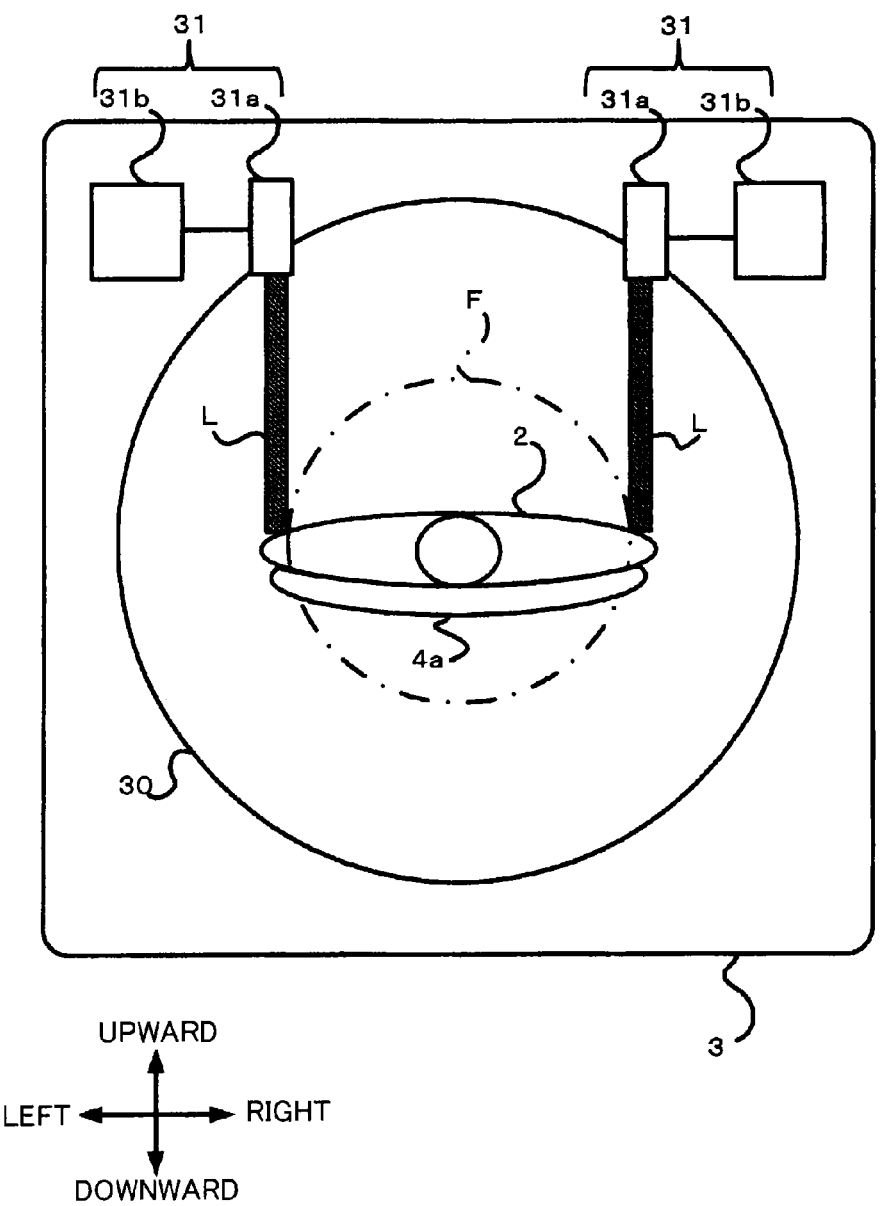
FIG. 6 is a drawing to supplement the description of the flow chart pertaining to Embodiment 1.

Next, a method of setting the field of view according to the X-ray CT apparatus 1 pertaining to the present embodiment is described with reference to FIG. 3, FIG. 5, and FIG. 6.

First, information regarding the body shape or the imaging region of the subject 2 is input by an examiner from the console 5, etc. The setting part 51 reads the value of the field of view F corresponding to the input information from a plurality of values regarding the field of view, and sets the field of view F (S10).

Based on the set results in S10, the moving mechanism 31b causes the light emission part 31a to move to a location where the light L is projected such that it touches the outer circumference of the field of view F (S11).

Thereafter, the console 5 controls the couch 4 and arranges the top board 4a on which the subject 2 is placed into the opening 30 (S12).

The light emission part 31a projects the light L such that it touches the outer circumference of the field of view F that has been set in S10 (S13). It should be noted that either of steps S12 or S13 may take place first.

By confirming the projected state in S13, the examiner is able to confirm the field of view F (S14). That is, as shown in FIG. 3, if the light L is projected to a location where the light L does not strike (or touches) the subject 2, it is determined that at least the imaging region is within the field of view F. On the other hand, as in FIG. 6, if the light L is projected onto a location where the light L strikes the subject 2, it is determined that the imaging region is possibly outside the field of view F.

<Action and Effect>

The actions and effects of a computed tomography apparatus such as the X-ray CT apparatus pertaining to the present embodiment are described.

The computed tomography apparatus comprises the couch 4 that moves the top board 4a on which the subject 2 is placed. The gantry 3 comprises a light projection part 31. The setting part 51 sets the field of view with respect to the subject 2. The controller 52 controls the light projection parts 31 and causes light indicating the set field of view to be projected.

More specifically, the light projection part 31 comprises the light emission part 31a that generates light and the moving mechanism 31b that moves the light emission part 31a. The controller 52 controls the moving mechanism 31a based on the set field of view, thereby projects light from the light emission part 31a such that the light indicates the field of view (for example, such that it touches the outer circumference of the field of view).

According to such a configuration, the examiner is able to recognize the field of view by the light from the light projection part 31. That is, the positional relationship between the imaging region and the field of view in a real space may be confirmed at the time of determining the imaging region.

Moreover, multiple light projection parts 31 are provided. For example, there are two light projection parts 31 on the right and left sandwiching the center of the opening 30 in the upper part of the gantry 30.

Therefore, even if the subject 2 is placed in an off-set manner on the top board 4a, it is possible to verify whether or not the imaging region is within the field of view by the light from the light projection parts 31 of the right and left. That is, the positional relationship of the imaging region and the field of view may be confirmed at the time of determining the imaging region.

<Modification Example 1 of Embodiment 1>

Figure 7:
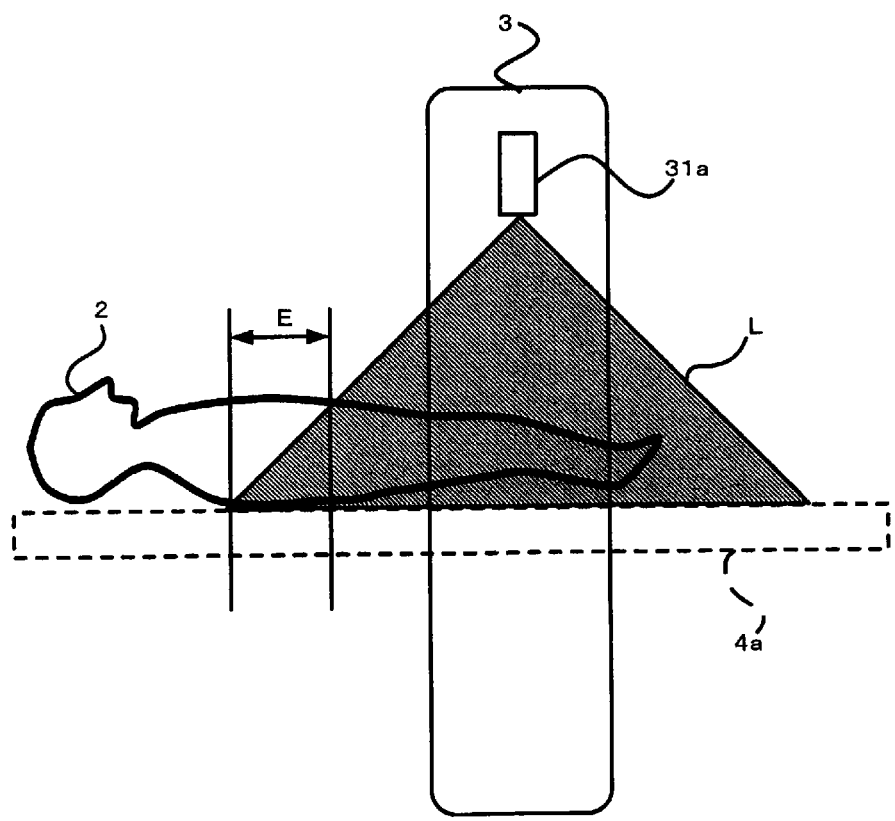
FIG. 7 is a drawing describing the premise of the configuration pertaining to Modification Example 1 in Embodiment 1.
Figure 8:
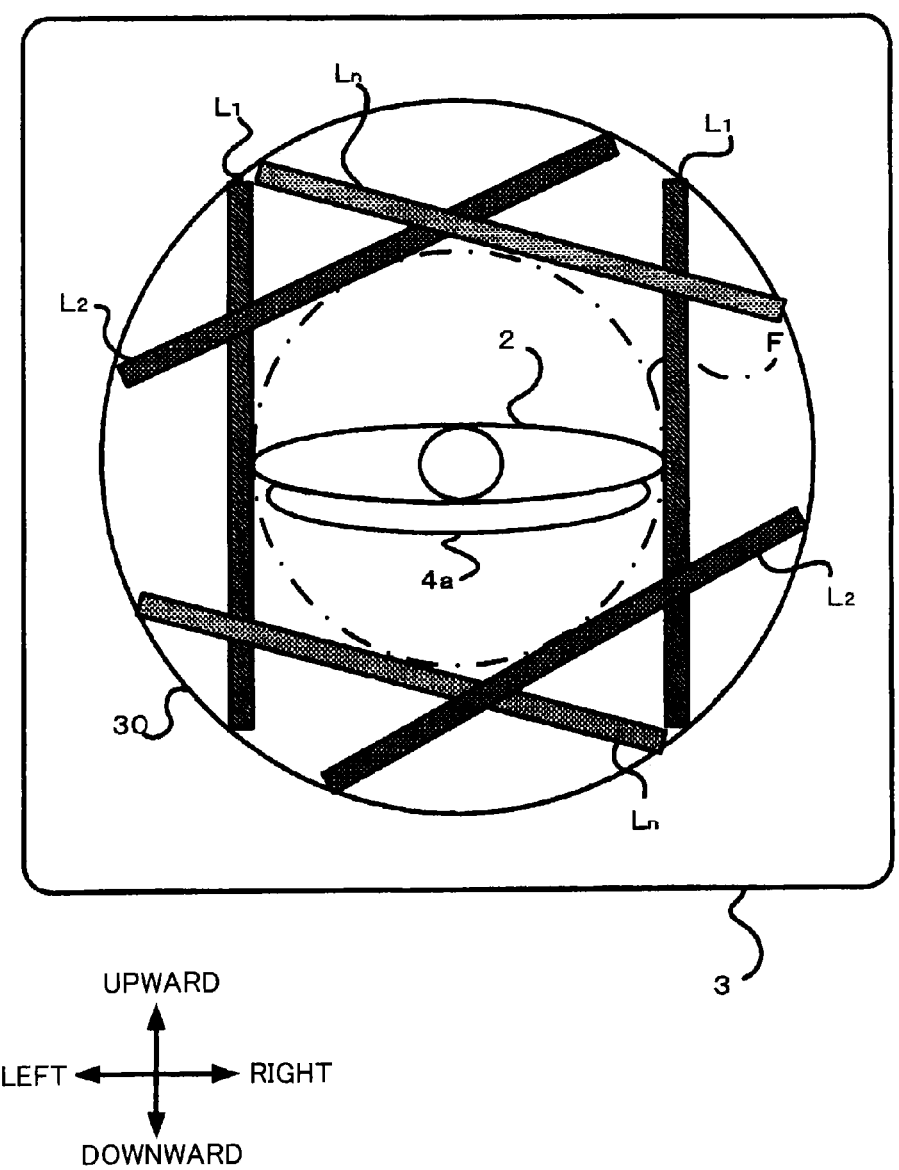
FIG. 8 is a drawing showing the configuration of a gantry pertaining to Modification Example 1 in Embodiment 1.
Figure 9:
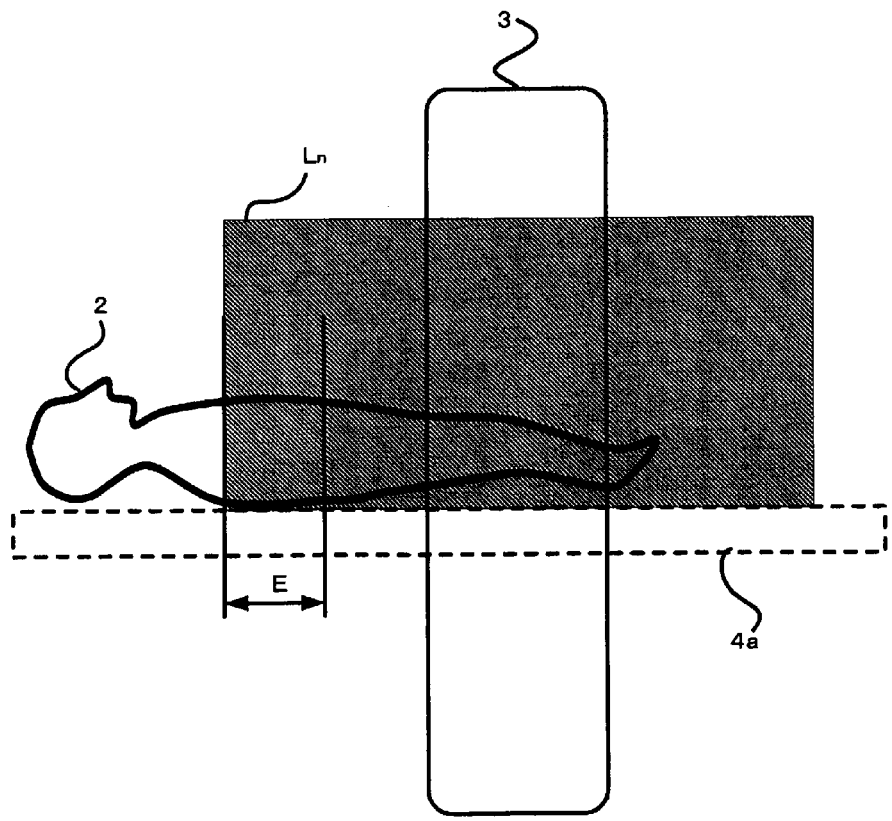
FIG. 9 is a drawing showing the configuration of a gantry pertaining to Modification Example 1 in Embodiment 1.

Modification Example 1 of Embodiment 1 is described with reference to FIGS. 7 through 9. Mention of the configuration of the light projection part 31 (light emission part 31a, moving mechanism 31b) is omitted in FIG. 8 and FIG. 9.

For example, when conducting helical scanning with the configuration of Embodiment 1, even if the subject 2 is located at the start position for imaging (the position to start X-ray imaging), there is a possibility that the light from the light emission part 31a will not be projected onto a portion of the imaging region (range E shown in FIG. 7) (ref. FIG. 7). Therefore, it is impossible to confirm whether or not the entire region subjected to imaging is within the field of view.

To solve this problem in the present modification example, causing the light projection part 31 to rotate around the opening 30 by the rotation mechanism provided in the gantry 3 and showing the field of view makes it possible to confirm whether or not the entire imaging region is within the field of view.

That is, by causing the light projection part 31 to rotate, light from the light projection part 31 is projected such that it draws a cylindrical trajectory around the subject (ref. $L_k$ (k=1 to n) in FIG. 8 and FIG. 9. $L_k$ indicates the light projected by the light projection part 31 from a position in the circumference of the opening part 30. FIG. 9 virtually shows the region where the light $L_k$ is projected). That is, it becomes possible to show the field of view from various directions with respect to the subject 2. Accordingly, the positional relationship between the imaging region and the field of view in a real space may be confirmed at the time of determining the imaging region regardless of the position of the subject 2.

<Modification Example 2 of Embodiment 1>

Modification Example 2 of Embodiment 1 is described with reference to FIG. 10A and FIG. 10B.

It is sufficient for the projected light L to indicate the field of view F (to cause the examiner to recognize the field of view F).

Figure 10A:
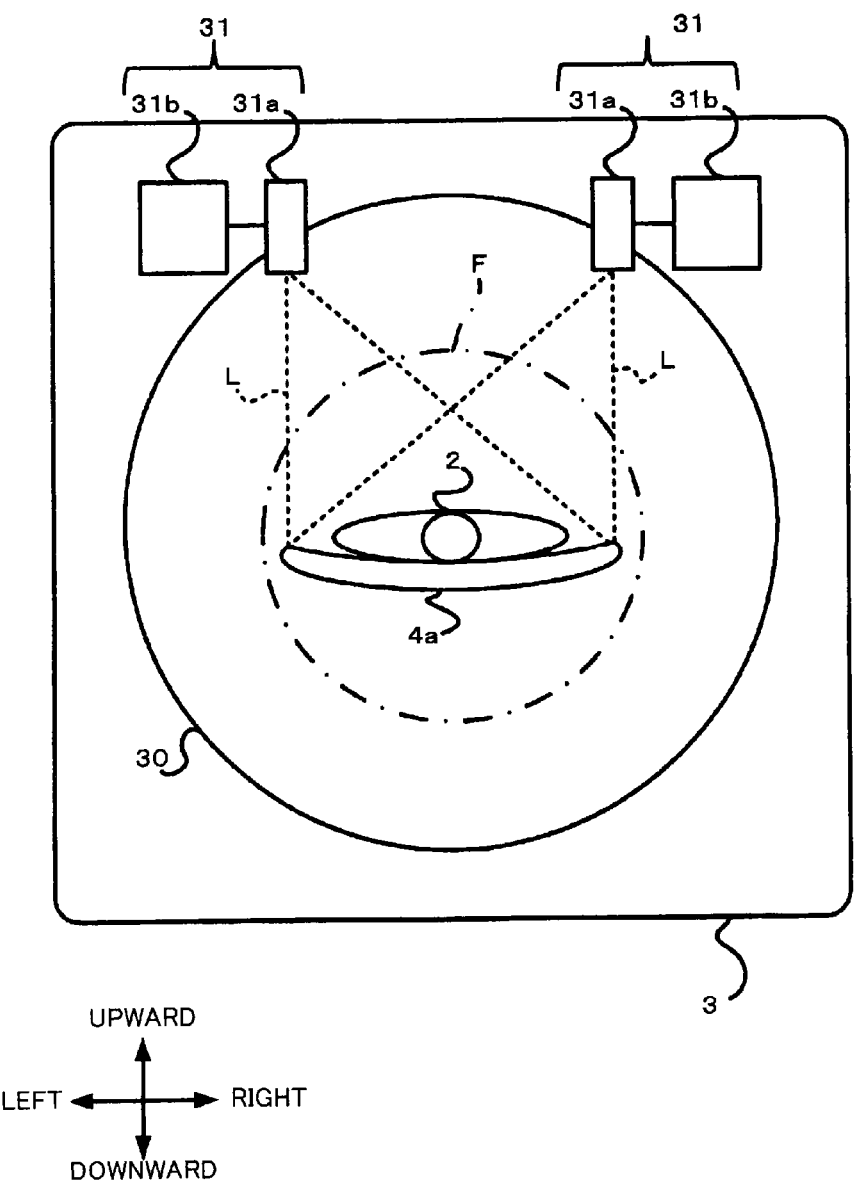
FIG. 10A is a drawing showing the configuration of a gantry pertaining to Modification Example 2 in Embodiment 1.

For this, as shown in FIG. 10A, the controller 52 may control the light projection parts 31 such that light from the light emission part 31a is projected into the set field of view F. FIG. 10A shows an example in which light L from each of two light projection parts 31 is projected into the field of view F. Specifically, the light L from one of the light projection parts 31 is projected as light spreading in the left and right directions such that it strikes both ends of the top board 4a in the left and right directions (both ends are located within the field of view F) (as light spreading in the left and right directions in the field of view F). It should be noted that one end of the light L may be in touch with the outer circumference of the field of view F. By confirming whether or not the subject 2 is within the light L (whether the light L is striking the subject 2), the examiner is able to determine whether or not the subject 2 is within the field of view F. In FIG. 10A, the subject 2 is within the light L. That is, the examiner is able to determine that the subject 2 is in the field of view F. As described, according to the configuration of FIG. 10A, because the light L strikes the entire subject 2 within the field of view F, it is easy to identify whether or not the subject 2 is within the field of view F.

Figure 10B:
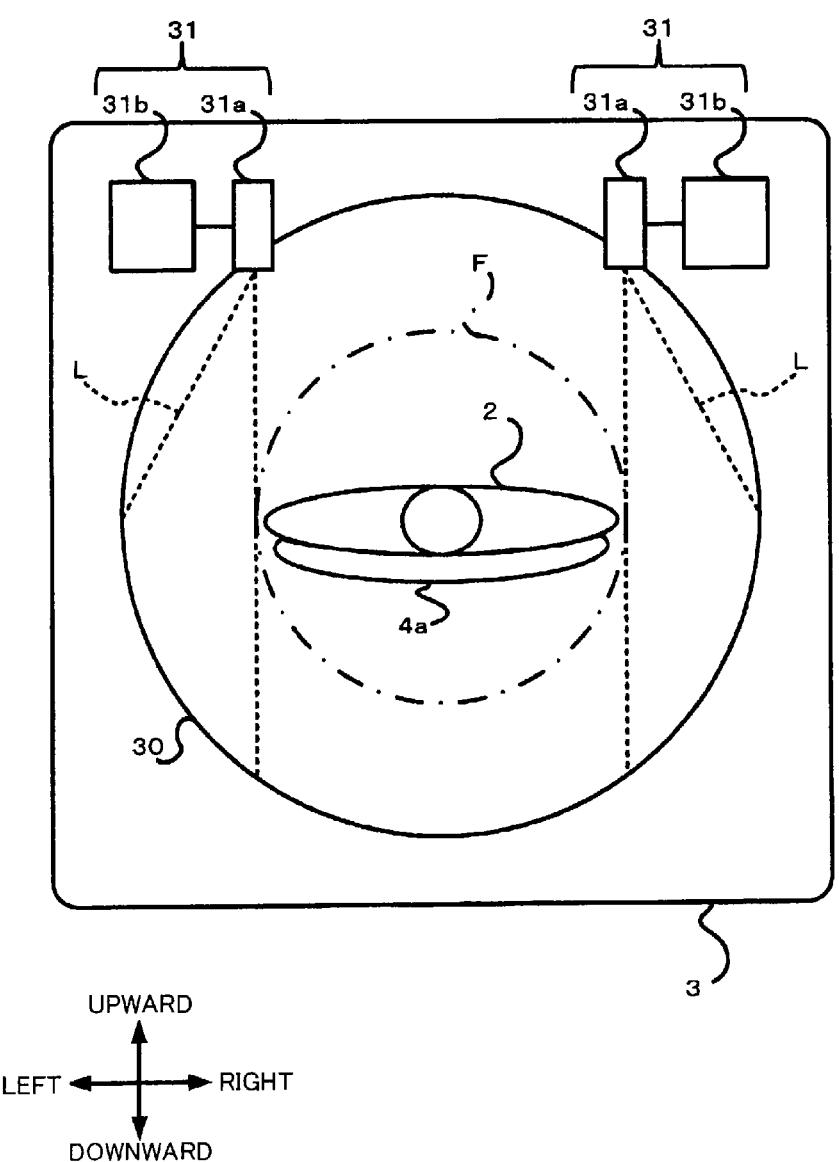
FIG. 10B is a drawing showing the configuration of a gantry pertaining to Modification Example 2 in Embodiment 1.

Alternatively, as shown in FIG. 10B, the controller 52 may control the light projection parts 31 to make it possible to project light from the light emission part 31a outside the set field of view F in addition to touching the outer circumference of the set field of view F. FIG. 10B shows an example in which the light L from each of the two light projection parts 31 is projected outside the field of view F. Specifically, the light L from one of the light projection parts 31 is projected as light spreading in the left and right directions such that it strikes the inner surface of the opening 30 outside the field of view F. It should be noted that one end of the light L is touching the outer circumference of the field of view F (ref. FIG. 10B). The examiner is able to identify the region of the subject 2 located outside the field of view F by confirming whether or not the light L is striking the subject 2. Conversely, if the light is not striking the subject 2, the examiner can determine that the subject 2 is within the field of view F. In FIG. 10B, the light L is not striking the subject 2. That is, the examiner can determine that the subject 2 is within the field of view F. Furthermore, if the subject 2 is located outside the field of view F, because the light L strikes its entirety, the region located outside the field of view F may easily be recognized.

As described above, the light L from the light emission part 31a in the present modification example is light spreading in the left and right directions. Such light L may be realized, for example, by providing a slit spreading in the left and right directions in the light projection part 31. Or, the light L may also be realized by swaying the light emission part 31a in the light projection part 31.

<Embodiment 2>

The computed tomography apparatus pertaining to Embodiment 2 is described with reference to FIGS. 11 through 13. In the present embodiment, the X-ray CT apparatus 1 is used as a computed tomography apparatus for the explanation. It should be noted that mentions of the configurations that are the same as in Embodiment 1 are omitted. In the present embodiment, at the initial position, the distance between light projected from the light emission part 31a and the center of the opening is denoted by α (ref. FIG. 12).

Figure 11:
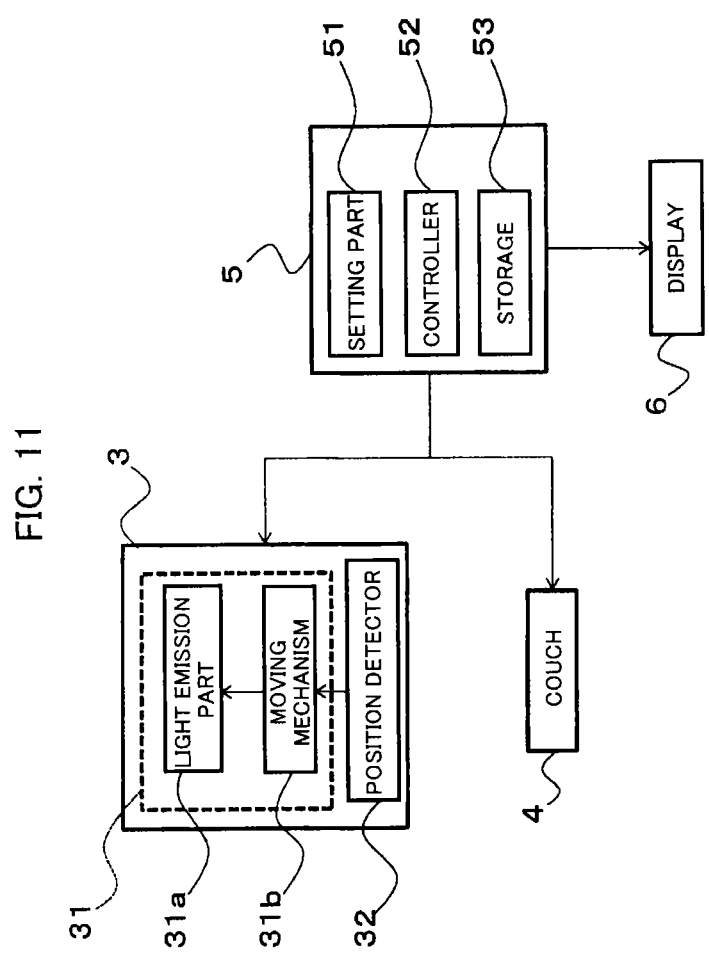
FIG. 11 is a block diagram showing the internal configuration of an X-ray CT apparatus pertaining to Embodiment 2.
Figure 12:
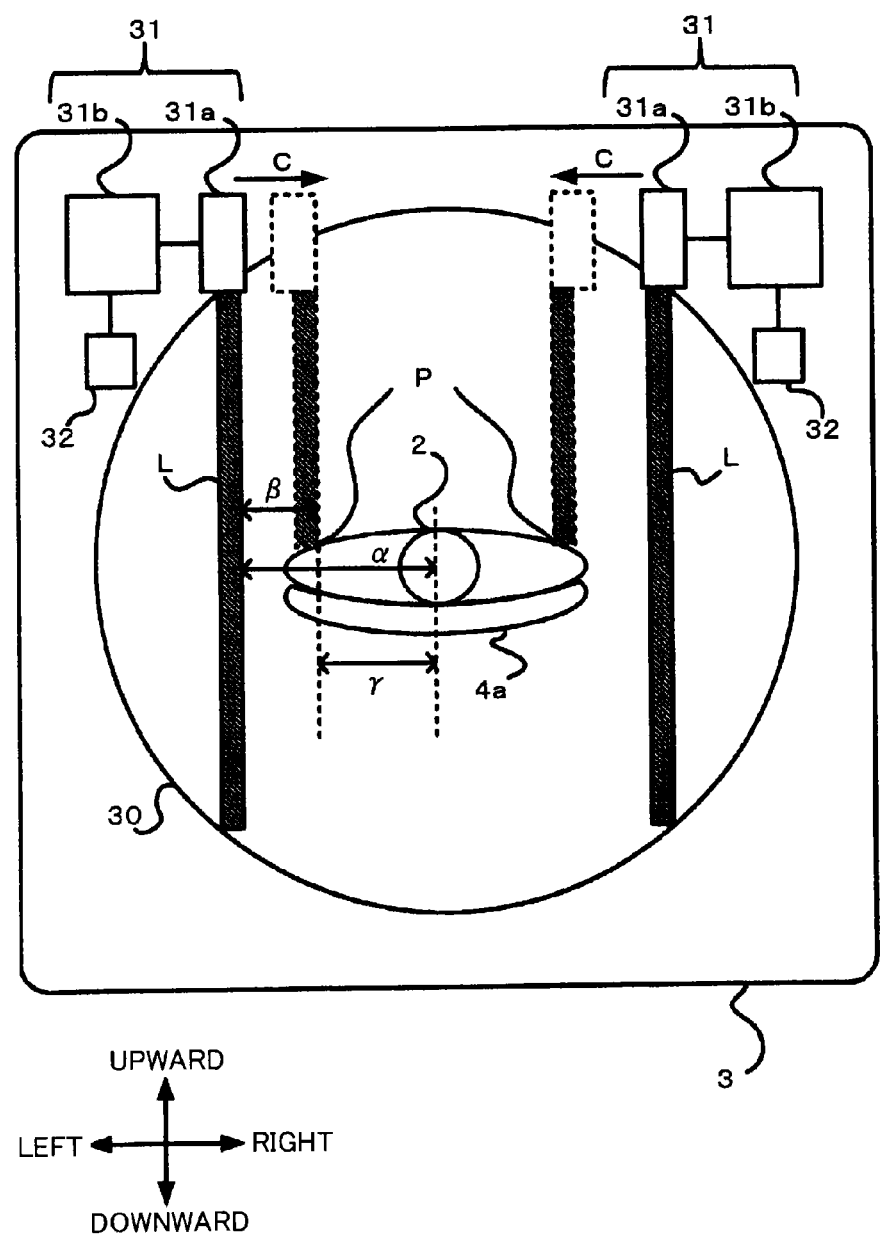
FIG. 12 is a drawing showing the configuration of a gantry pertaining to Embodiment 2.
Figure 13:
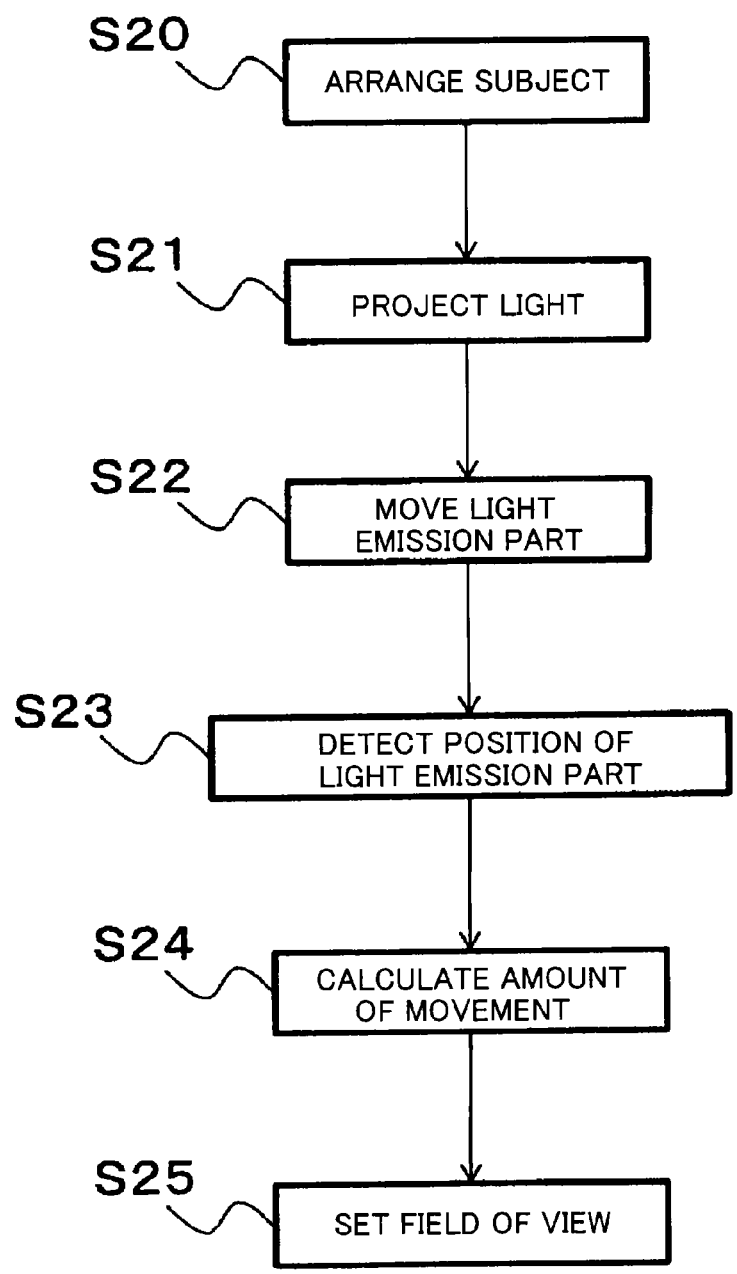
FIG. 13 is a flow chart showing the outline of the processing pertaining to Embodiment 2.

As shown in FIG. 11 and FIG. 12, in the present embodiment, position detectors 32 are provided in the gantry 3. The position detector 32 detects the position of the light emission part 31a. The position detector 32 comprises, for example, an encoder.

The moving mechanism 31b in the present embodiment causes the light projection part 31 to move in the radial direction of the opening (left and right directions in FIG. 12). The moving mechanism 31b is operated and controlled by the controller 52.

The setting part 51 in the present embodiment calculates the amount of movement of the light emission part 31a, based on the detection result by the position detector 32, and sets the field of view based on the detection result. The amount of movement is the value indicating the amount of movement of the light emission part 31a from the initial position.

Specifically, the distance between the two light projection parts 31 is gradually narrowed (direction of arrow C in FIG. 12) by the moving mechanism 31b. Subsequently, when the light from the light emission part 31a is projected onto the position P (the position at the end part of the region including the imaging region, ref. FIG. 12), via an input instruction from the examiner, the position detector 32 sends, to the setting part 51, information indicating the position of the light emission part 31a at that moment. The setting part 51 calculates the amount of movement β of the light emission part 31a from the position from the light emission part 31a and the initial position. Subsequently, the setting part 51 obtains the distance $\gamma$ ($\gamma=\alpha-\beta$) from the center of the opening 30 to the position P based on the distance α and the distance β and sets, as the field of view, the region centered at the center position of the opening 30 with the radius γ.

As described, the position detector 32 and the function for calculating the amount of movement of the light emission part 31a in the setting part 51 correspond to a "calculator" in the present embodiment.

It should be noted that the amount of movement of the light emission part 31a may be calculated by the setting part 51, based on a control signal by which the controller 52 operates the moving mechanism 31b. In this case, the controller 52 and the function for calculating the amount of movement of the light emission part 31a in the setting part 51 correspond to a "calculator."

<Operation>

A method of setting the field of view by the X-ray CT apparatus 1 pertaining to the present embodiment is described with reference to FIG. 13.

When an instruction to start imaging is received, the console 5 causes the top board 4a on which the subject 2 is placed to be arranged in the opening 30 (S20).

The light emission part 31a located at an initial position projects light L (S21). It should be noted that either of steps S20 or S21 may take place first.

The examiner gives an instruction, via the gantry 3, etc., to narrow the distance between the light projection parts 31 until the light L is projected onto the position P while checking the projection position of the light L (S22).

When the light L is projected on the position P, based on an instruction from the examiner, the position detector 32 detects the position P of the light emission part 31a at that moment (S23). The detection result by the position detector 32 is sent to the setting part 51.

The setting part 51 calculates the amount of movement β of the light emission part 31a based on the position P detected in S23 and the initial position of the light emission part 31a (S24).

Subsequently, the setting part 51 sets the field of view, based on the amount of movement β calculated in S24 and the distance α from the initial position to the center of the opening 30 (S25). That is, the setting part 51 obtains the distance $\gamma$ ($\gamma=\alpha-\beta$) from the center of the opening 30 to the position P, and sets the region centered at the center position of the opening 30 with the radius γ, as the field of view.

It should be noted that, as shown in FIG. 10B, it is also possible to project the light L as light spreading in the left and right directions such that it strikes the inner surface of the opening 30 outside the field of view F.

Alternatively, as shown in FIG. 10A, the light L may be projected as light spreading in the left and right directions within the field of view F. In this case, the position detector 32 detects the position P of the light emission part 31a at the moment when the subject 2 enters into the light L based on an instruction from the examiner. The setting part 51 may set the field of view based on the position P by conducting processes in S24 and S25.

<Action and Effect>

The actions and effects of a computed tomography apparatus such as the X-ray CT apparatus pertaining to the present embodiment are described.

The moving mechanism 31*b* of the computed tomography apparatus moves the light emission part 31*a* in the radial direction of the opening 30. The calculator calculates the amount of movement of the light emission part 31*a* by the moving mechanism 31*b*. The setting part 51 sets the field of view based on the calculation result of the calculator.

According to this configuration, the field of view in accordance with the imaging part of the subject 2 may be set without preliminarily setting an arbitrary field of view. Therefore, it is possible to set such that the subject 2 comes into the field of view at the time of determining the position of the subject 2. Furthermore, it becomes possible to set the field of view for imaging a site within the body of the subject 2 (for example, the region surrounding a heart in a torso).

<Embodiment 3>

The configuration of the computed tomography apparatus pertaining to Embodiment 3 is described with reference to FIGS. 14 through 16. In the present embodiment, the X-ray CT apparatus 1 is used as a computed tomography apparatus for the explanation. It should be noted that mentions of the configurations that are the same as in Embodiment 1 and Embodiment 2 are omitted.

Figure 14:
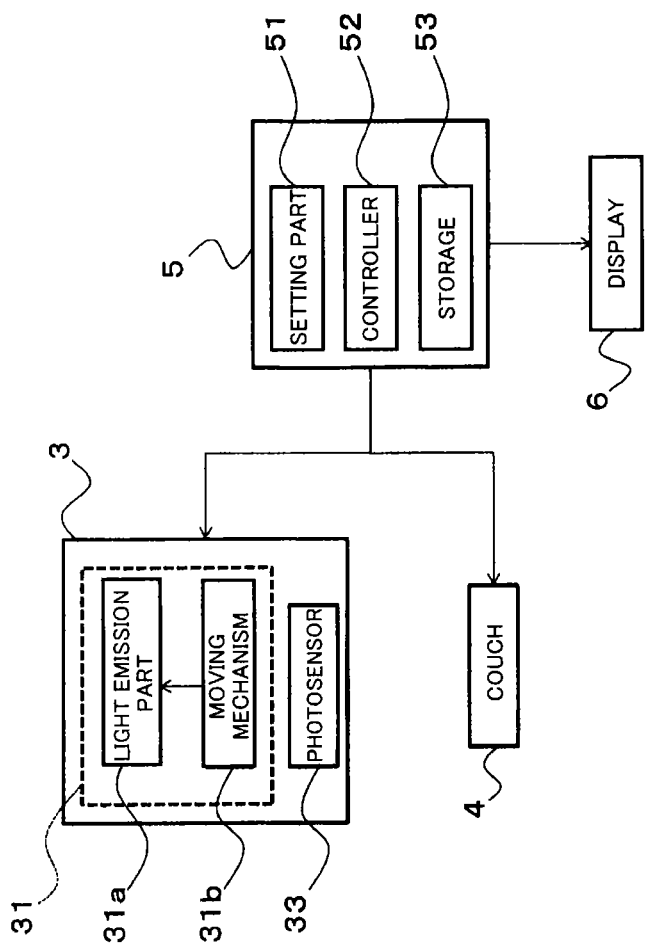
FIG. 14 is a block diagram showing the internal configuration of an X-ray CT apparatus pertaining to Embodiment 3.
Figure 15:
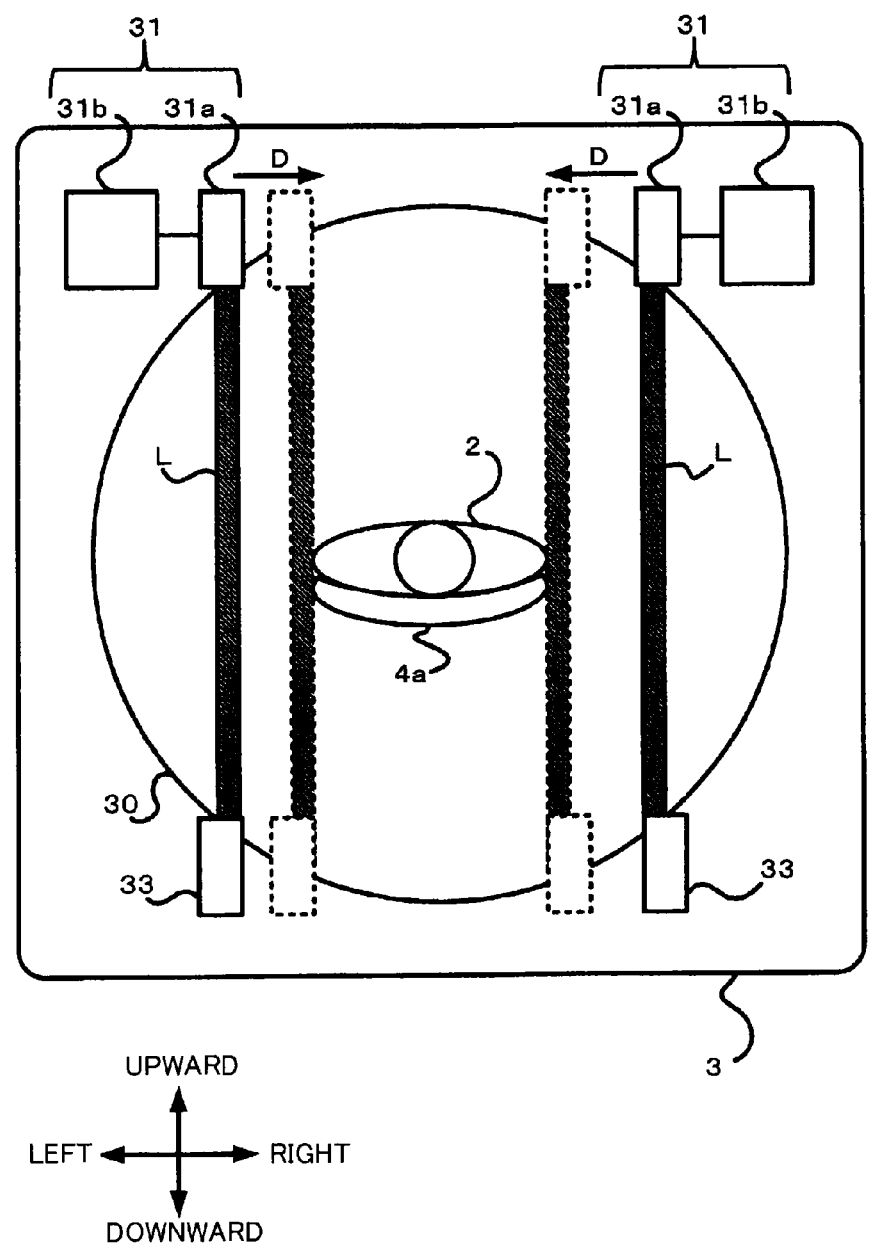
FIG. 15 is a drawing showing the configuration of a gantry pertaining to Embodiment 3.
Figure 16:
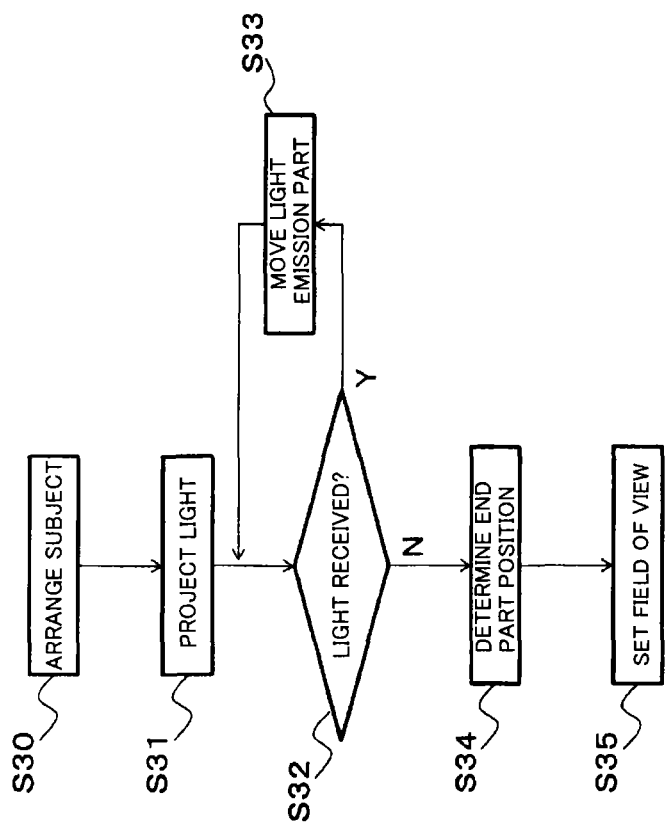
FIG. 16 is a flow chart showing the outline of processing pertaining to Embodiment 3.

As shown in FIG. 14 and FIG. 15, photosensors 33 are provided in the gantry 3 in the present embodiment. The photosensor 33 is a sensor for detecting light from the light projection part 31 (light emission part 31*a*). As a photosensor 33, for example, a photo detector is used. The light projection part 31 (light emission part 31*a*) and the photosensor 33 are arranged in oppositely facing locations sandwiching the opening 30.

The moving mechanism 31*b* in the present embodiment moves the light projection part 31 and the photosensor 33 in the radial direction (left and right directions in FIG. 15) of the opening 30.

The setting part 51 in the present embodiment specifies the end part position of the subject 2 based on the detection result of the light by the photosensor 33 and sets the field of view based on the specified result.

Specifically, the distance between two light projection parts 31 (between the photosensors 33) is gradually narrowed by the moving mechanism 31*b* (direction of arrow D in FIG. 15). While the distance is being narrowed, the photosensor 33 detects the light from the light projection part 31. Subsequently, when the light from the light projection part 31 is no longer detected by the photosensor 33 (that is, when the light from the light projection part 31 strikes the subject), the setting part 51 determines the position of the light projection part 31 (or the position of the photosensor 33) immediately prior to that moment as the end part position of the subject 2. Subsequently, the setting part 51 sets, as a radius, the distance from the position where light is last detected by the photosensor 33 (the end part position of the subject 2) to the center of the opening 30, and sets the region centered at the center position of the opening 30 with this radius as the field of view.

<Operation>

Next, the method of setting the field of view according to the X-ray CT apparatus 1 pertaining to the present embodiment is described with reference to FIG. 16.

When an instruction to start imaging is received, the console 5 causes the top board 4*a* on which the subject 2 is placed to be arranged in the opening 30 (S30).

The light emission part 31*a* projects light L toward the photosensor 33 provided in the gantry 3 (S31). It should be noted that either of steps S30 or S31 may take place first.

If the light L is received by the photosensor 33 (in case of Y in S32), it means that there is no blocking object (subject 2) between the light emission part 31*a* and the photosensor 33. In this case, the moving mechanism 31*b* gradually narrows the distance between the light projection parts 31 (between the photosensors) (S33). It should be noted that while the distance between the light projection parts 31 (between the photosensors 33) is being narrowed, the light L projected toward the photosensor 33 from the light emission part 31*a* may be constant or intermittent.

On the other hand, when the distance between the light projection parts 31 (between the photosensors 33) is being narrowed, there is a case in which the light L is not received by the photosensor 33 (in case of N in S32). This is caused by the fact that the light from the light emission part 31*a* is blocked by the subject 2 and the light is not received by the photosensor 33. In this case, the setting part 51 determines the position of the light projection part 31 (or the position of the photosensor 33) immediately prior to that moment as the end part position of the subject 2.

The setting part 51 sets the field of view by defining the distance from the position determined in S34 to the center of the opening 30 as the radius of the field of view (S35). That is, the setting part 51 regards the distance from the center of the opening 30 to the position determined in S34 as the radius, and sets the region centered at the center position of the opening 30 with this radius as the field of view.

<Actions and Effects>

The actions and effects of a computed tomography apparatus such as the X-ray CT apparatus pertaining to the present embodiment are described.

The gantry 3 of the computed tomography apparatus comprises the photosensor 33 that detects light from the light projection part 31. The light projection part 31 and the photosensor 33 are arranged at opposite facing locations sandwiching the opening 30. The moving mechanism 31*b* moves the light projection part 31 and the photosensor 33 in the direction that is perpendicular to the connecting direction of these and is the radial direction of the opening 30. The setting part 51 determines the end part position of the subject 2 based on the detection result of the light by the photosensor 33, and sets the field of view based on the determined result.

According to the configuration, the field of view in accordance with the imaging region of the subject 2 may be obtained without preliminarily designating the field of view. Therefore, it is possible to set such that the subject 2 comes into the field of view when determining the position of the subject 2.

<Modification Example of Embodiments 2 and 3>

In Embodiments 2 and 3, configurations for setting the field of view using two light projection parts 31 are described; however, configurations are not limited to these.

Figure 17:
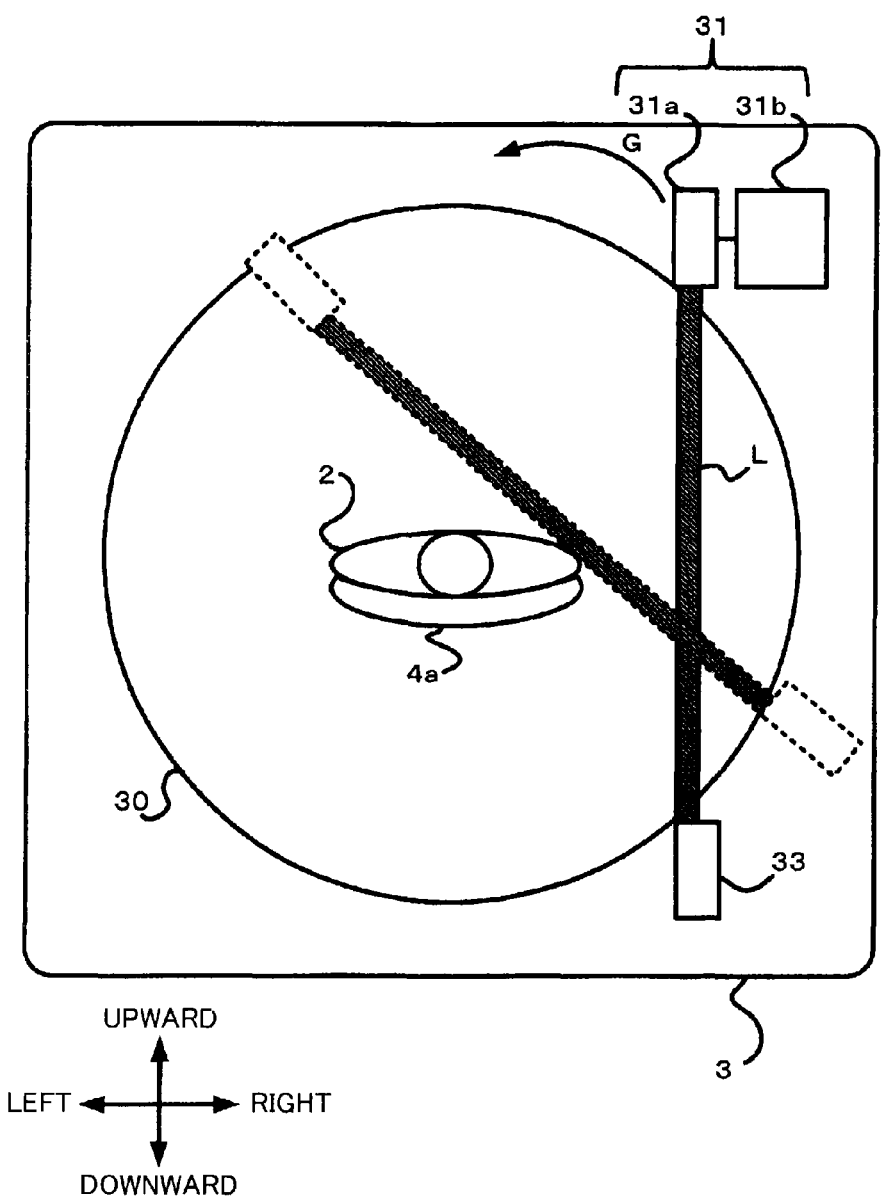
FIG. 17 is a drawing showing the configuration of a gantry pertaining to modification examples in Embodiments 2 and 3.

For example, as shown in FIG. 17, the computed tomography apparatus in the present modification example comprises one light projection part 31 and one photosensor 33. The distance between the subject 2 and the light L from the light projection part 31 is gradually narrowed by the moving mechanism 31*b* while rotating the light projection part 31 and the photosensor 33 by the rotation mechanism in the direction of the arrow G in FIG. 16 (ref. Modification Example 1 in Embodiment 1). Subsequently, the position at which the light L touches the subject 2 is determined as the end part position of the subject 2 and the field of view is set by the setting part 51. It should be noted that information such as the rotating angle of the light projection part 31, the positional variation of the light projection part 31 and the photosensor 33 caused by the rotation, the width of the subject 2, etc. is used to determine the end part position.

According to this configuration, a simplified structure with one light projection part 31 makes it possible to obtain the field of view in accordance with the imaging region of the subject 2. Therefore, it is possible to set such that the subject 2 comes into the field of view at the time of determining the position of the subject 2.

<Modification Example>

The configuration of the above embodiment is not limited to an X-ray CT apparatus. The configuration is also applicable to any computed tomography apparatus (for example, a PET apparatus, SPECT, and an MRI apparatus) for which it is required to set the field of view.

Moreover, in the above Embodiment 2 and 3, configurations in which the distance between two light emission parts 31a is gradually narrowed are described; however, configurations are not limited to these. For example, the field of view may be set by arranging the light emission part 31a in the upward direction of the center position of the opening 30 as the initial position and widening the distance between the two light emission parts 31a in the outward direction (for example, the left and right directions in FIG. 12) of the opening part 30 from the initial position.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

EXPLANATION OF SYMBOLS

1 X-ray CT apparatus
2 subject
3 gantry
4 couch
5 console
6 display
30 opening
31 light projection part
31a light emission part
31b moving mechanism
51 setting part
52 controller

What is claimed is:

1. A computed tomography apparatus for imaging the inside of a subject by processing, using a computer, data acquired by irradiating radiation onto the subject, the computed tomography apparatus comprising:
    a couch that moves a top board on which the subject is placed,
    a gantry that comprises an opening into which the top board is inserted,
    a light projection part provided in the gantry that projects light,
    a setting part that sets a field of view that corresponds to a region of the computed tomography imaging, a width of the field of view being adjusted according to input information, and the field of view being set with respect to the subject,
    a controller that controls the light projection part to project the light such that a boundary of the light corresponds to a boundary of the field of view and a distance between points on the boundary of the light equals the width of the field of view, and
    circuitry configured to signal the controller to adjust the boundary of the light in accordance with the input information, and then, after the adjusting of the boundary of the light, signaling the setting part to set the field of view in accordance with the adjusted boundary of the light.

2. The computed tomography apparatus according to claim 1, wherein
    the light projection part comprises
        a light emission part that generates the light, and
        a moving mechanism that moves the light emission part to perform the adjusting of the distance between the points on the boundary of the light to equal the width of the field of view, and
    the controller controls the moving mechanism based on the width of the field of view and causes the light from the light emission part to be projected such that the boundary of the light corresponds to the boundary of the field of view, and that the distance between the points on the boundary of the light equals the width of the boundary of the field of view.

3. The computed tomography apparatus according to claim 1, wherein the controller controls the light projection part to project the light such that the boundary of the field of view is an outer circumference of the field of view.

4. The computed tomography apparatus according to claim 1, wherein the controller controls the light projection part to project the light within the field of view.

5. The computed tomography apparatus according to claim 1, wherein the controller controls the light projection part to project the light outside the field of view and the boundary of the field of view is an outer circumference of the field of view.

6. The computed tomography apparatus according to claim 2, wherein the controller controls the light projection part to project the light such that the boundary of the light corresponds to an outer circumference of the field of view.

7. The computed tomography apparatus according to claim 2, wherein the controller controls the light projection part to project the light within the field of view.

8. The computed tomography apparatus according to claim 2, wherein the controller controls the light projection part to project the light outside the field of view and the boundary of the field of view is an outer circumference of the field of view.

9. The computed tomography apparatus according to claim 2, wherein
    the moving mechanism moves the light emission part in a radial direction of the opening of the gantry and the moving mechanism includes a calculator that calculates an amount of movement of the light emission part by the moving mechanism to generate a calculation result, and
    the setting part sets the field of view based on the calculation result by t calculator.

10. The computed tomography apparatus according to claim 2, further comprising:

a photosensor that is provided in the gantry and detects light from the light emission part, wherein the photosensor is arranged diametrically opposed to the light emission part across the opening of the gantry the moving mechanism moves the light emission part and the photosensor in a radial direction of the opening of the gantry, and the setting part determines an end part location of the subject, based on a detection of the light by the photosensor and sets the field of view based on the determined end part location of the subject.

11. The computed tomography apparatus according to claim 1, wherein a plurality of the light projection parts are provided.

12. The computed tomography apparatus according to claim 1, wherein the gantry comprises a rotation mechanism that rotates the light projection part along a periphery of the opening of the gantry during a time without the irradiating of the radiation onto the subject.

* * * * *